United States Patent [19]

Rattner

[11] Patent Number: 5,251,630

[45] Date of Patent: Oct. 12, 1993

[54] PRESSURE PULSE GENERATOR HAVING AN ELECTROMAGNETIC PRESSURE PULSE SOURCE

[75] Inventor: Manfred Rattner, Grossenseebach, Fed. Rep. of Germany

[73] Assignee: Siemens Aktiengesellschaft, Munich, Fed. Rep. of Germany

[21] Appl. No.: 897,063

[22] Filed: Jun. 11, 1992

[30] Foreign Application Priority Data

Jul. 12, 1991 [DE] Fed. Rep. of Germany ....... 4123160

[51] Int. Cl.⁵ ............................................. A61B 17/22
[52] U.S. Cl. ................... 128/660.03; 128/24 EL; 367/175
[58] Field of Search ........ 128/24 AA, 24 EL, 660.03; 367/142, 174, 175

[56] References Cited

U.S. PATENT DOCUMENTS

| | | | |
|---|---|---|---|
| 4,766,888 | 8/1988 | Oppelt | 128/24 EL |
| 4,796,608 | 1/1989 | Koehler | 128/24 EL |
| 4,928,672 | 5/1990 | Grasser et al. | |
| 5,137,014 | 8/1992 | Boehm | 128/24 EL |
| 5,191,560 | 2/1993 | Lobentanzer et al. | 367/175 |

FOREIGN PATENT DOCUMENTS 3739390 6/1989 Fed. Rep. of Germany.
4039408 6/1991 Fed. Rep. of Germany.

*Primary Examiner*—Ruth S. Smith
*Attorney, Agent, or Firm*—Hill, Steadman & Simpson

[57] ABSTRACT

A pressure pulse generator has an electromagnetic pressure pulse source which includes a coil arrangement for driving an electrically conductive membrane. The coil arrangement is divided into a first annular coil section and a second annular coil section, the second annular coil section surrounding the first annular coil section. The respective ends of the coil sections are maintained at respective electrical potentials so that, upon activation of the pressure pulse generator to generate pressure pulses, voltage arcing between the respective ends of the coil sections and components adjacent thereto is precluded.

12 Claims, 2 Drawing Sheets

PRESSURE PULSE GENERATOR HAVING AN ELECTROMAGNETIC PRESSURE PULSE SOURCE

BACKGROUND OF THE INVENTION

1. Field of the Invention

The present invention is directed to a pressure pulse generator having an electromagnetic pressure pulse source, and in particular to such a pressure pulse generator having a pressure pulse source of the type having an electrically conductive membrane and an electrical coil arrangement for driving the membrane, with a central bore, for accepting a component such as the ultrasound application of an ultrasound locating system, extending through the membrane and through the coil arrangement, with a further component, such as a housing, arranged in the region of the outer edge of the coil arrangement.

2. Description of the Prior Art

Acoustic pressure pulse generators of the type described above are used for medical purposes for, for example, treating stone, bone and tumor pathologies. Such acoustic pulse generators are also used for non-medical purposes. In any case, the pressure pulse generator is acoustically coupled by a suitable coupling element to the subject which is to be charged with pressure pulses, and the subject and the pressure pulse generator are aligned relative to each other so that the pressure pulses pass through the target region of the subject.

European Application 0 301 360, corresponding to U.S. Pat. No. 4,928,672 describes a pressure pulse generator of this type. In such pulse generators, as is conventional, the housing as well as the ultrasound head are at ground potential. The coil is a flat coil having spiral turns, and has an inner terminal and an outer terminal. Either the outer terminal, which is adjacent the housing, or the inner terminal, which is adjacent the ultrasound applicator, is also at ground potential. The other terminal of the coil arrangement is supplied with high voltage upon activation of the pressure pulse source, to cause the generation of pressure pulses by interaction with the flexible, electrically conductive membrane.

This arrangement has the risk of voltage arcing between the inner terminal of the coil arrangement and the ultrasound applicator, or between the outer terminal of the coil arrangement and the housing. Because such voltage arcing not only decreases the useful life of the pressure pulse generator, but also can lead to destruction of the ultrasound applicator, an insulating distance of sufficient size to avoid voltage arcing is provided between the outer terminal of the coil arrangement and the housing, or between the inner terminal of the coil arrangement and the ultrasound applicator. If an ultrasound applicator of a specific diameter is to be used, an increased need for installation space arises as a consequence of the aforementioned insulating distance which must be provided, regardless of whether the outer terminal or the inner terminal of the coil arrangement is at ground potential.

SUMMARY OF THE INVENTION

It is an object of the present invention to provide a pressure pulse generator of the type described above wherein the risk of voltage arcing is avoided, or is at least reduced without an increased need for installation space.

The above object is achieved in accordance with the principles of the present invention in a pressure pulse generator having an electromagnetic pressure pulse source with an electrically conductive membrane and an electrical coil arrangement, wherein a bore for accepting a component extends through the membrane and the coil arrangement and/or a further component is arranged in the region of the outer edge of the coil arrangement, in which the coil arrangement is formed by a first coil section surrounding the bore and a second coil section surrounding the first coil section. Each coil section has an inner end and an outer end. Upon activation of the pressure pulse source to generate pressure pulses, the outer end of the first coil section and the inner end of the second coil section are at a first potential, the inner end of the first coil section is at a second potential, and the outer end of the second coil section is at a third potential. The second potential substantially corresponds to the potential of the component which is received in the bore, and the third potential substantially corresponds to that of the further component which is disposed in the region of the outer edge of the coil arrangement.

Due to the subdivision of the coil into two annular coil sections, the end of the inner coil section which is situated in the region of the component received in the bore, and the end of the outer coil section which is situated in the region of the component disposed at the outside edge of the coil arrangement, can be at the same potential as the respectively adjacent component, so that voltage arcing is precluded without having to observe an insulating distance between the respective end of the coil section and the adjacent component. In the pressure pulse generator disclosed herein, therefore, enhanced reliability against voltage arcing is achieved without an increased need for installation space. Insofar as the permissible operating voltage for the pressure pulse generator is not exceeded, there is no risk of voltage arcing between the adjacent ends of the coil section, which are at the first potential, even through the first potential deviates from the second and third potentials, because the ends which are at the first potential are already disposed a sufficiently large distance from other components.

Although a decreased risk of arcing is present even when the differences between the first and second, and second and third, potentials are slight, in a preferred embodiment of the invention these potential differences are in the kilovolt range, i.e., at least approximately 1 kV or more. Preferably the first potential deviates from the second potential and deviates from the third potential in the same direction, i.e., the first potential is either more negative than both the second and third potentials, or the first potential is more positive than both the second and third potentials. This results in the insulation outlay being reduced, as may possibly be required between the component disposed in the bore and the component situated in the region of the outer edge of the coil arrangement. This insulation outlay is completely eliminated in a further preferred embodiment of the invention, wherein the second potential is substantially the same as the third potential. If both the second potential and the third potential are ground potential, the technical outlay for the electrical generator required for the voltage supply to the pressure pulse generator is reduced. Although it is theoretically possible to select opposite directions of current flow for the first and second coil sections, it is preferable to select the winding direction of the coil sections, and to select the second and third potentials, so that the current flow in the coil sections is in the same direction, because this results in an improved efficiency compared to oppositely directed current flows.

The component which is accepted in the bore may be the ultrasound applicator of an ultrasound locating system, and the component situated in the region of the outer edge of the coil arrangement may be the housing for the pressure pulse generator.

Although other windings arrangements are possible, the electrical coil arrangement used in the context of the pressure pulse generator disclosed herein preferably has spiral turns.

DESCRIPTION OF THE PREFERRED EMBODIMENTS

Figure 1:
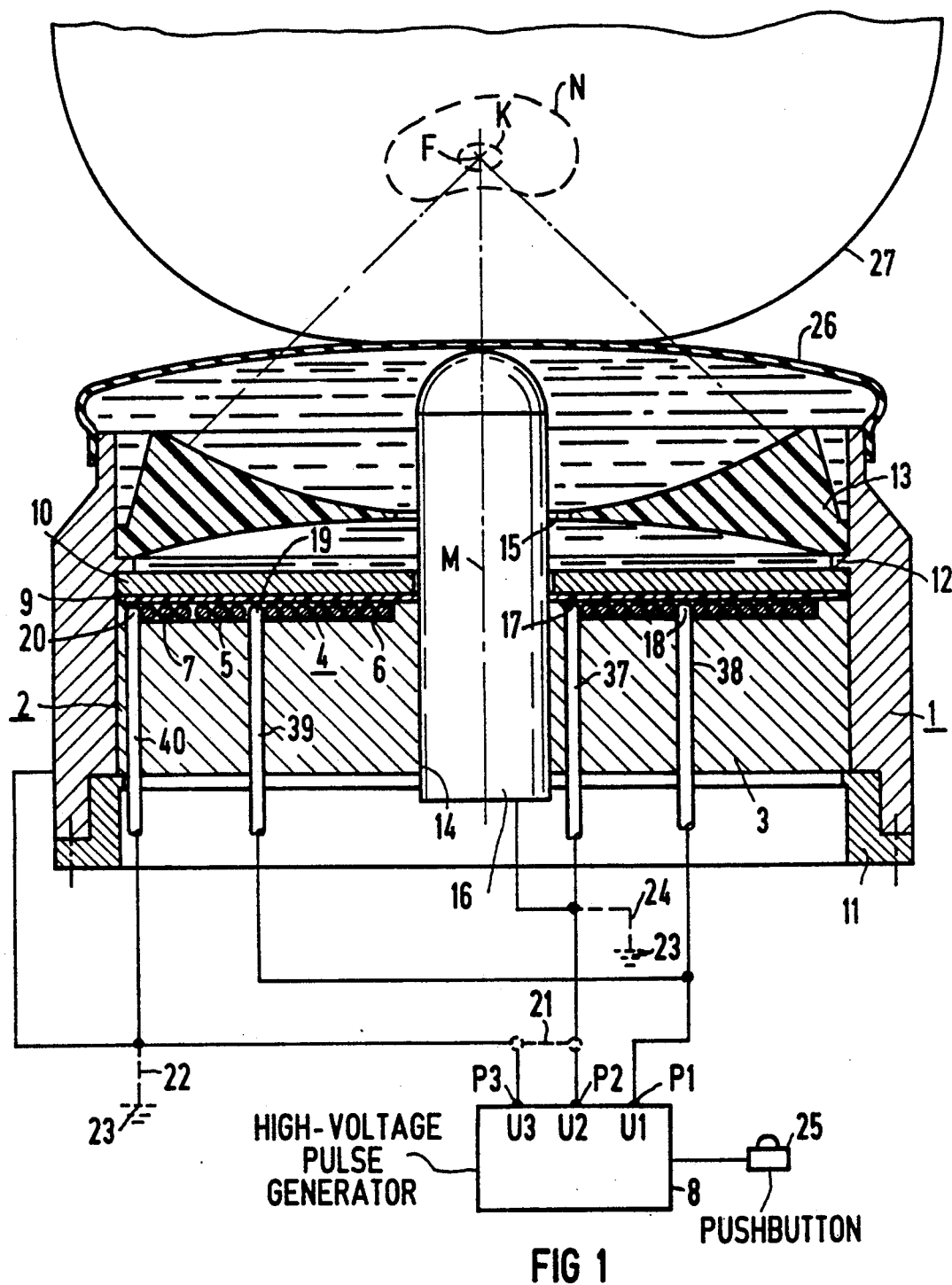
FIG. 1 is a longitudinal sectional view of a pressure pulse generator constructed in accordance with the principles of the present invention, in the form of a shockwave generator for generating focused shockwaves.

A pressure pulse generator constructed in accordance with the principles of the present invention is shown in FIG. 1, embodied as a shockwave generator for the in vivo disintegration of calculi in a patient. The shockwave generator has a tubular housing 1 in which a shockwave source, generally referenced 2, is received. The housing contains a liquid acoustic propagation medium in which a pressure pulse emitted by the shockwave source 2 steepens into a shockwave, however, "shockwave" and "pressure pulse" can be considered interchangeable in the context of the present invention, as can "pressure pulse source" and "shockwave source."

The shockwave source 2 has an annular coil arrangement 4 with helical windings disposed on a planar seating surface of a coil carrier 3, one such winding turn being referenced 5. The coil carrier 3 consists of electrically insulating material, for example aluminum oxide ceramic. The space between the windings 5 of the coil arrangement 4 is filled with an electrically insulating casting resin in a known manner. The coil arrangement 4 is subdivided into two annular coil sections, an inner section 6 and an outer coil section 7. As described below, these coil sections are connected to a high-voltage pulse generator 8.

An annular planar membrane 10 consisting of an electrically conductive material, for example copper, is disposed opposite the side of the coil arrangement 4 which faces away from the coil carrier 3, with an insulating foil 9 being interposed between the coil arrangement 4 and the membrane 10. The membrane 10, the insulating foil 9 and the coil carrier 3 together with the coil arrangement 4 are pressed against an annular projection 12 provided in the interior of the housing 1, by means of a tube section 11 introduced into the housing 1 and having a radially outwardly directed flange at its end facing away from the coil carrier 3. Two screws, schematically indicated by dot-dashed lines, hold the tube section 11 against the housing 1. The membrane 10 is thereby pressed liquid-tight against the projection 12, possibly with a suitable sealant (not shown).

A biconcave, acoustic lens 13 consisting, for example, of polystyrol is disposed against the side of the projection 12 facing away from the membrane 10.

The thicknesses of the insulating foil 9 and of the membrane 10 as well as the wire thickness of the coil arrangement 4 are shown exaggerated in FIG. 1 for clarity.

The space limited by the side of the membrane 10 facing away from the coil arrangement 4 and by the housing 1 is closed by an elastic application bellows 26, this volume being filled with the aforementioned liquid, acoustic propagation medium for the shockwaves, for example water.

The coil carrier 3 and the positive lens 13 have respective central bores 14 and 15 having center axes coinciding with the center axis M of the shockwave generator. An ultrasound applicator 16 of a known ultrasound locating system extends through the bores 14 and 15, and thus also through the central openings of the membrane 10 and the coil arrangement 4. The ultrasound applicator 16, which is displaceable in the direction of the center axis M and is rotatable around the center axis M using a known adjustment system (not shown), is received liquid-tight in the bore 14 of the coil carrier 3. Sealants can be provided as needed.

The inner coil section 6 has an inner end 17 and an outer end 18. The outer coil section 7 has an inner end 19 and an outer end 20. These ends are respectively connected to the high-voltage pulse generator 8 via lines 37, 38, 39 and 40. This pulse generator 8 has three poles P1, P2 and P3. The outer end 18 of the inner coil section 6 and the inner end 19 of the outer coil section 7 are both electrically connected to the first pole P1. The inner end 17 of the inner coil section 6 and the ultrasound applicator 16 (such as the housing thereof) are electrically connected to the pole P2. The outer end 20 of the outer coil section 7 and the housing 1 are electrically connected to the pole P3.

When the shockwave source 2 is activated to generate a shockwave, with a push button 25 connected to the high-voltage pulse generator 8, the poles P1, P2 and P3 at least briefly are respectively placed at a first potential U1, a second potential U2 and a third potential U3. The potentials U1, U2 and U3 are selected so that a pulse-like current flows both through the inner coil section 6 and through the outer coil section 7. The difference in potential between the poles P1 and P2, and the difference in potential between the poles P1 and P3, are in the kilovolt range. The times at which the poles P1 through P3 are the respective potentials U1 through U3 are selected so that the pulse-like currents flow substantially simultaneously through the inner and outer coil sections 6 and 7, and have substantially the same pulse duration. This can easily be achieved by constructing the high-voltage pulse generator 8 so that the poles P2 and P3 are constantly at the respective potentials U2 and U3, and only the pole P1 is placed at the potential U1 for the desired pulse duration of the current in order to generate a shockwave. Other electrical techniques for achieving this result will be devisable by those skilled in the art based on the present disclosure.

As a consequence of the pulse-like currents flowing through the coil sections 6 and 7, the coil sections 6 and 7 rapidly build up magnetic fields, which induce eddy currents in the regions of the membrane 10 respectively disposed opposite the coil sections 6 and 7. These eddy currents are in a direction opposite to the current flowing through the corresponding coil section. These eddy currents have magnetic fields associated therewith which have a direction opposite to the direction of the magnetic fields associated with the current flowing through the coil sections 6 and 7. As a consequence of the resulting repulsion forces, the membrane 10 is rapidly moved away from the coil arrangement 4, resulting in an initially planar pressure pulse being introduced into the water adjacent the membrane 10, serving as the acoustic propagation medium. This pressure pulse is focused onto a focal zone F, disposed on the center axis M of the shockwave generator, by means of the positive lens 13, as indicated with dot-dash lines in FIG. 1. The focused pressure pulse propagates in the water situated between the positive lens 13 and the bellows 26, and passes through the bellows 26 into the body of a patient 27 to be treated. With the assistance of the ultrasound locating system, the shockwave generator is pressed by means of the bellows 26 against the body of the patient 27 to be treated in a position so that a calculus K to be disintegrated, for example a stone in a kidney N, is situated in the focal zone F. The calculus K can be disintegrated with a series of pressure pulses into fragments which are so small that they can be eliminated in a natural manner. As noted above, the pressure pulses emanating from the membrane 10 intensify into shockwaves as they propagate through the propagation medium, as a result of the non-linear compression properties of the propagation medium and the tissue of the patient 27. The shockwaves are pressure pulses having an extremely steep leading front.

As a consequence of the subdivision of the coil arrangement 4 into the two coil sections 6 and 7, the end 20 adjacent the housing 1 can be placed at the same potential by providing an electrical connection therebetween, and similarly the end 17 and the adjacent ultrasound applicator 16 can be placed at the same potential by means of an electrical connection therebetween. Voltage arcing at these locations is thus precluded, so that insulating measures which increase the installation space, particularly which increase the diameter of the shockwave generator, are not required. It is clear that no voltage arcing at normal operating voltages can occur between the ends 18 and 19 of the coil sections 6 and 7 or between the corresponding lines 38 and 39 which are at a potential which is different than that of the housing 1 and the ultrasound applicator 16.

It is preferable that the poles P2 and P3 be at equipotential, i.e., that the potentials U2 and U3 be the same, as indicated in FIG. 1 by the dashed line connection 21 connecting the poles P2 and P3. In this embodiment, the high-voltage generator 8 is simplified, because it must offer only two potentials. A further simplification can be achieved by making the potentials U2 and U3 equal to ground potential 23, as also indicated in FIG. 1 by a grounding line 22 shown with dashed lines. If the potentials U2 and U3 deviate from each other, it is possible to make one of the potentials U2 or U3 equal to ground potential. This possibility is also indicated in FIG. 1 with a further grounding line 24 shown with dashed lines, connecting the pole P2 to ground potential 23.

In the above-described exemplary embodiment, the winding direction of the coil sections 6 and 7 is selected so that, taking the potentials U2 and U3 into consideration, an identically directed current flow, for example in a clockwise direction, occurs in both coil sections 6 and 7. Optimum efficiency of the shockwave generator is achieved thereby, because the coil sections 6 and 7 do not have a significant disadvantageous influence on each other. In order to achieve an identically directed current flow in the coil sections 6 and 7, these must be wound with respectively opposite winding directions if the potentials U2 and U3 are the same. This is shown in FIG. 2, which is a schematic plan view onto the coil carrier 3 together with the coil arrangement 4, with the membrane 10 and the insulating foil 9 removed.

Figure 2:
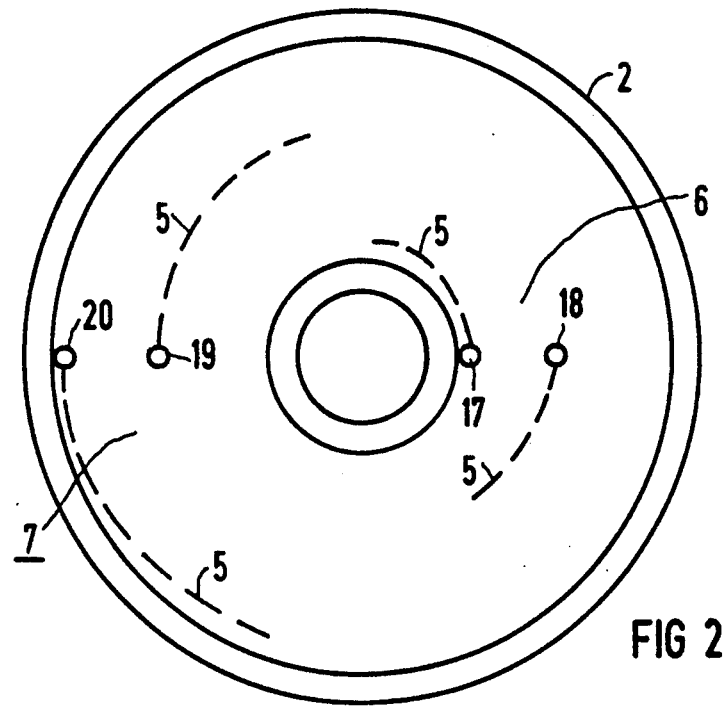
FIG. 2 is a schematic illustration of the coil arrangement of the shockwave generator of FIG. 1.

If both the inner end 17 of the inner coil section 6 and the outer end 20 of the outer coil section 7 are at ground potential 23, a clockwise current flow direction results for the embodiment shown in FIG. 2, given a positive potential U1. A counter-clockwise current flow direction would result given a negative potential U1.

Figure 3:
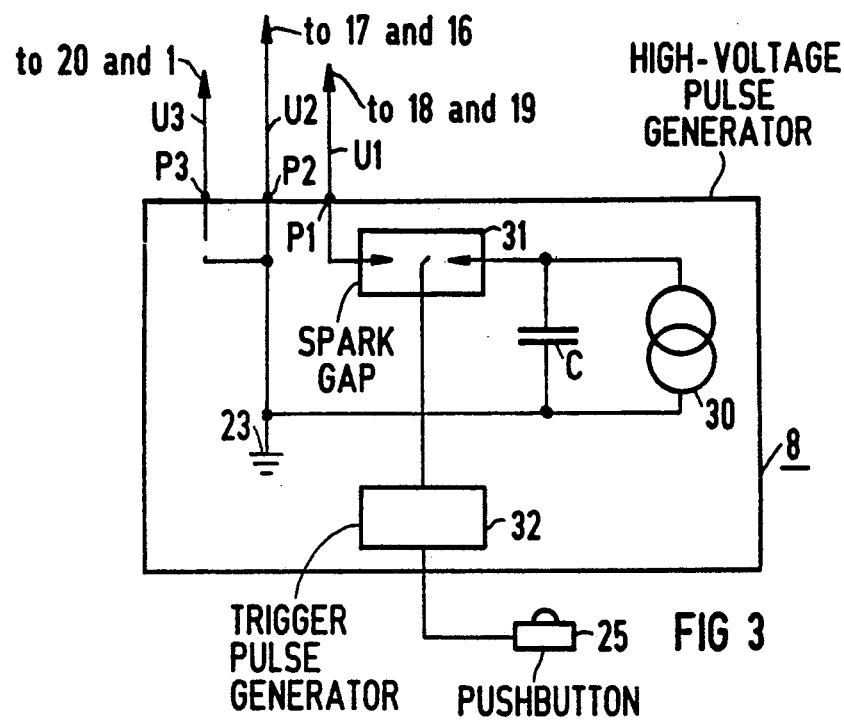
FIG. 3 is a block diagram of a circuit for a high-voltage pulse generator for use in the shockwave generator shown in FIG. 1.

A possible embodiment of the high-voltage pulse generator 8 is shown in FIG. 3 in block circuit form, with the potentials U2 and U3 both being ground potential. The high-voltage pulse generator 8 of FIG. 3 contains a high-voltage capacitor C, which can be charged to high voltage, for example +20 kV or −20 kV, by a charging current source 30. One terminal of the high-voltage capacitor C is connected to one primary electrode of a triggerable spark gap 31. The other primary electrode of the spark gap 31 is connected to the pole P1 which carries the potential U1. The pole P1 is in turn connected to the outer end 18 of the inner coil section 6 and to the inner end 19 of the outer coil section 7, as shown in FIG. 1. The other terminal of the high-voltage capacitor C is connected to the poles P2 and P3, which thus are at the same potential. The connecting line 21, indicated with dashed lines in FIG. 1 can be eliminated in this embodiment. The poles P2 is connected to the inner end 17 of the inner coil section 6 and to the ultrasound applicator 16. The pole P3 is connected to the outer end 20 of the outer coil section 7 and to the housing 1.

The connection of the poles P2 and P3 to ground potential 23 is undertaken by connecting the terminal of the high-voltage capacitor C, which is connected to the poles P2 and P3, to ground potential 23. The grounding lines 22 or 24 shown in FIG. 1 are thus not needed in the embodiment of the high-voltage pulse generator 8 of FIG. 3.

The push button 25 is connected to a trigger pulse generator 32, to which the trigger electrode of the spark gap 31 is connected. Upon actuation of the push button 25, the trigger pulse generator 32 supplies a trigger pulse to the trigger electrode of the spark gap 31, resulting in ignition of the spark gap 31. The electrical energy stored in the high-voltage capacitor C then suddenly discharges into the coil arrangement 4, causing the pulse-like current required for generating a shockwave to flow through the coil sections 6 and 7.

In general, the coil sections 6 and 7, taking the differences in potential between their ends 17, 18, 19 and 20 into account, are dimensioned so that the same surface current density (i.e., the number of conductors permeated by the pulse-like current per unit of area) exists for both coil sections 6 and 7. This results in a uniform drive of the membrane 10, which in turn results in the pressure pulses introduced into the water having a pressure which is substantially location independent in the immediate proximity of the membrane 10. For the purpose of influencing the pulse shape of the generated pressure pulses, however, it is possible to intentionally produce different surface current densities, for example, to compensate for imaging errors of the positive lens 13. For example, different surface current densities can be achieved by employing coil sections having different inductivity.

Separate lines 38 and 39 as shown in the exemplary embodiment need not necessarily be provided for the outer end 18 of the inner coil section 6 and for the inner end 19 of the outer coil section 7. It is possible to short-circuit the ends 18 and 19 and provide a single line for connecting the ends 18 and 19 to the high-voltage pulse generator 8.

The above exemplary embodiment has been described in the context of a shockwave source which initially generates planar shockwaves, which are then focused by means of the positive lens 13. The inventive concept disclosed herein, however, can be employed in any electromagnetic pressure pulse source, including such pressure pulse sources which generate unfocused shockwaves. The inventive concept can also be employed in so-called self-focusing electromagnetic shockwave sources, wherein the shockwaves are focused by providing the shockwave source itself with a spherical shape, or by means of a suitably shaped reflector.

Moreover, the exemplary embodiment has been set forth in the context of a pressure pulse generator for the disintegration of calculi. It is clear that the pressure pulse generator disclosed herein can be employed for any desired medical and non-medical purpose.

Although modifications and changes may be suggested by those skilled in the art, it is the intention of the inventor to embody within the patent warranted hereon all changes and modifications as reasonably and properly come within the scope of his contribution to the art.

I claim as my invention:

1. A pressure pulse generator comprising:
   a housing filled with an acoustic propagation medium;
   an electromagnetic pressure pulse source disposed in said housing and having an electrical coil and a flexible membrane disposed for interacting with said acoustic propagation medium;
   drive means for electrically driving said coil for causing rapid displacement of said flexible membrane from said coil for emitting a pressure pulse into said acoustic propagation medium, said drive means having a plurality of outputs connected to said coil and respectively at first, second and third electrical potentials;
   said coil and said membrane each having a central opening; and
   said coil consisting of first and second coil sections each having an inner end and an outer end, said first coil section surrounding said central opening and said second coil section surrounding said first coil section, said outer end of said first coil section and said inner end of said second coil section being at said first potential, said inner end of said first coil section being at said second potential, and said outer end of said second coil section being at said third potential.

2. A pressure pulse generator as claimed in claim 1 wherein said first, second and third electrical potentials are respectively different potentials, and wherein the difference between said first potential and said second potential and the difference between said first potential and said third potential are both at least one kilovolt.

3. A pressure pulse generator as claimed in claim 1 wherein said second potential and said third potential both deviate from said first potential in the same direction.

4. A pressure pulse generator as claimed in claim 3 wherein said second potential is substantially equal to said third potential.

5. A pressure pulse generator as claimed in claim 1 wherein said first and second coil sections have respective winding directions and wherein said second and third potentials are selected with respect to said winding directions for causing current flow in the same direction in both said first and second coil sections upon activation of said drive means.

6. A pressure pulse generator as claimed in claim 1 wherein said electrical coil has a plurality of spiral turns.

7. A pressure pulse generator comprising:
   a housing filled with an acoustic propagation medium;
   an electromagnetic pressure pulse source disposed in said housing and having an electrical coil and a flexible membrane disposed for interacting with said acoustic propagation medium;
   drive means for electrically driving said coil for causing rapid displacement of said flexible membrane from said coil for emitting a pressure pulse into said acoustic propagation medium, said drive means having a plurality of outputs connected to said coil and respectively at first, second and third electrical potentials; first and second electrical components;
   said coil and said membrane each having a central opening receiving said first component and said coil having an outer edge disposed in a region of said second component which is at said third potential; and
   said coil consisting of first and second coil sections each having an inner end and an outer end, said first coil section surrounding said central opening and said second coil section surrounding said first coil section, said outer end of said first coil section and said inner end of said second coil section being at said first potential, said inner end of said first coil section being at said second potential, and said outer end of said second coil section being at said third potential.

8. A pressure pulse generator as claimed in claim 7 wherein said first component is an ultrasound applicator of an ultrasound locating system.

9. A pressure pulse generator as claimed in claim 7 wherein said second component is said housing.

10. A pressure pulse generator comprising:
    a housing filled with an acoustic propagation medium;
    an electromagnetic pressure pulse source disposed in said housing and having an electrical coil and a flexible membrane disposed for interacting with said acoustic propagation medium;
    drive means for electrically driving said coil for causing rapid displacement of said flexible membrane from said coil for emitting a pressure pulse into said acoustic propagation medium, said drive means having a plurality of outputs connected to said coil and respectively at first, second and third electrical potentials; first and second electrical components;
    said coil and said membrane each having a central opening receiving said first component which is at said second potential and said coil having an outer edge disposed in a region of said second component; and said coil consisting of first and second coil sections each having an inner end and an outer end, said first coil section surrounding said central opening and said second coil section surrounding said first coil section, said outer end of said first coil section and said inner end of said second coil section being at said first potential, said inner end of said first coil section being at said second potential, and said outer end of said second coil section being at said third potential.

11. A pressure pulse generator as claimed in claim 10 wherein said first component is an ultrasound applicator of an ultrasound locating system.

12. A pressure pulse generator as claimed in claim 10 wherein said second component is said housing.

* * * * *